(12) United States Patent
Evans

(10) Patent No.: US 12,285,583 B2
(45) Date of Patent: Apr. 29, 2025

(54) INFLATABLE PORTS, CATHETER ASSEMBLIES INCLUDING INFLATABLE PORTS, AND METHODS THEREOF

(71) Applicant: C. R. Bard, Inc., Franklin Lakes, NJ (US)

(72) Inventor: John G. Evans, South Jordan, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 1177 days.

(21) Appl. No.: 16/973,042

(22) PCT Filed: Jun. 20, 2019

(86) PCT No.: PCT/US2019/038321
§ 371 (c)(1),
(2) Date: Dec. 8, 2020

(87) PCT Pub. No.: WO2019/246448
PCT Pub. Date: Dec. 26, 2019

(65) Prior Publication Data
US 2021/0268250 A1    Sep. 2, 2021

Related U.S. Application Data

(60) Provisional application No. 62/687,433, filed on Jun. 20, 2018.

(51) Int. Cl.
*A61M 39/02*    (2006.01)
*A61M 39/04*    (2006.01)

(52) U.S. Cl.
CPC ........ *A61M 39/0208* (2013.01); *A61M 39/04* (2013.01); *A61M 2039/0232* (2013.01); *A61M 2039/0238* (2013.01)

(58) Field of Classification Search
CPC ...... A61M 39/0208; A61M 2039/0232; A61M 2039/0238; A61M 2039/0297;
(Continued)

(56) References Cited

U.S. PATENT DOCUMENTS

| 3,934,274 A | 1/1976 | Hartley, Jr. |
| 4,929,236 A | 5/1990 | Sampson |

(Continued)

FOREIGN PATENT DOCUMENTS

WO    2019246448 A1    12/2019

OTHER PUBLICATIONS

PCT/US2019/038321 filed Jun. 20, 2019 International Preliminary Report on Patentability dated Dec. 22, 2020.
PCT/US2019/038321 filed Jun. 20, 2019 International Search Report and Written Opinion dated Sep. 5, 2019.

*Primary Examiner* — Shefali D Patel
*Assistant Examiner* — William R Frehe
(74) *Attorney, Agent, or Firm* — Rutan & Tucker LLP (57) ABSTRACT

An inflatable port including a housing, a chamber in the housing, a septum over the chamber, a hollow stem extending from the housing, and a bladder around at least a portion of the housing. The chamber has a major opening and a minor opening. The septum is positioned over the major opening of the chamber and is fixed to the housing. The stem fluidly connects to the chamber by way of the minor opening of the chamber. The bladder is configured to increase a size of the inflatable port upon inflation of the bladder and decrease the size of the inflatable port upon deflation of the bladder. Also disclosed herein is a catheter assembly including the inflatable port, as well as a method related to the inflatable port and the catheter assembly.

15 Claims, 4 Drawing Sheets

(58) Field of Classification Search
CPC .......... A61M 2005/3114; A61M 39/04; A61M 39/0211; A61M 39/0214; A61M 39/0217; A61M 39/022; A61M 39/0223; A61M 39/0226; A61M 39/0229; A61M 2039/0235; A61M 2039/0247; A61M 2039/025; A61M 2039/0252; A61M 2039/0255; A61M 2039/0258; A61M 2039/0261; A61M 2039/0264; A61M 2039/027; A61M 2039/0273; A61M 2039/0276; A61M 2039/0279; A61M 2039/0282; A61M 2039/0285; A61M 2039/0288; A61M 2039/0294
See application file for complete search history.

(56) References Cited

U.S. PATENT DOCUMENTS

| | | | |
|---|---|---|---|
| 5,112,303 A * | 5/1992 | Pudenz | A61B 90/02 |
| | | | 604/502 |
| 7,351,233 B2 | 4/2008 | Parks | |
| 7,445,614 B2 | 11/2008 | Bunodiere et al. | |
| 8,821,373 B2 | 9/2014 | Schwab et al. | |
| 2006/0217668 A1 | 9/2006 | Schulze et al. | |
| 2009/0099538 A1 | 4/2009 | Paganon | |
| 2014/0148648 A1* | 5/2014 | Tycast | A61J 15/0065 |
| | | | 600/207 |
| 2017/0028185 A1 | 2/2017 | Wiley et al. | |

* cited by examiner

INFLATABLE PORTS, CATHETER ASSEMBLIES INCLUDING INFLATABLE PORTS, AND METHODS THEREOF

PRIORITY

This application is a U.S. national stage application of International Application No. PCT/US2019/038321, which claims the benefit of priority to U.S. Provisional Application No. 62/687,433, filed Jun. 20, 2018, each of which is incorporated by reference in its entirety into this application.

BACKGROUND

A clinician typically strives to minimize incision sizes and port-pocket sizes created in patients when implanting vascular access ports. Correspondingly smaller sized access ports are chosen to minimize scarring from implanting the ports. Unfortunately, smaller-sized ports may not always match the body habitus of the patients. This can result in access ports that cannot be located or palpated for infusion-set access.

If larger-sized access ports are implanted to avoid locating-and-palpating issues associated with infusion-set access, the larger-sized access ports might end up being too large for the patients—particularly following weight loss that is typical for cancer patients if they become cachectic. This can create cosmetic challenges for the patients, as well as possible skin erosion issues.

In view of the foregoing, a vascular access port is needed that minimizes port-placement scarring and avoids the locating-and-palpating issues associated with infusion-set access. Disclosed herein are inflatable access ports, catheter assemblies including the inflatable access ports, and methods thereof that address at least the foregoing.

SUMMARY

Disclosed herein is an inflatable port including, in some embodiments, a housing, a chamber within the housing, a septum over the chamber, a hollow stem extending from the housing, and a bladder around at least a portion of the housing. The chamber has a major opening and a minor opening. The septum is over the major opening of the chamber. The septum is fixed to the housing. The stem fluidly connects to the chamber by way of the minor opening of the chamber. The bladder is configured to increase a size of the inflatable port upon inflation of the bladder and decrease the size of the inflatable port upon deflation of the bladder.

In some embodiments, the bladder is fixed to the housing around the major and minor openings of the chamber. Fixing the bladder to the housing around the major opening of the chamber provides unobstructed needle access to the septum. Fixing the bladder to the housing around the minor opening of the chamber provides fluid communication between the chamber and the stem.

In some embodiments, the bladder is a needle penetrable, self-sealing bladder configured for inflation by way of penetration with a needle and injection with a fluid in a syringe.

In some embodiments, the bladder is a needle penetrable, self-sealing bladder configured for deflation by way of penetration with a needle and withdrawal of a fluid form the bladder into a syringe.

In some embodiments, the fluid is selected from a liquid including water or saline and a gas including air, nitrogen, or argon. In some embodiments, the fluid is sterile saline.

In some embodiments, the housing has a structural integrity for mechanically assisted pressurized injections to achieve a desired flow rate of injectant through the inflatable port.

Also disclosed herein is catheter assembly including, in some embodiments, an inflatable port, a catheter configured to fluidly connect to the inflatable port, and a catheter lock configured to lock the catheter on to the inflatable port. The inflatable port includes a housing, a chamber within the housing, a septum over the chamber, a hollow stem extending from the housing, and a bladder around at least a portion of the housing. The chamber has a major opening and a minor opening. The septum is over the major opening of the chamber. The septum is fixed to the housing. The stem fluidly connects to the chamber by way of the minor opening of the chamber. The bladder is configured to increase a size of the inflatable port upon inflation of the bladder and decrease the size of the inflatable port upon deflation of the bladder. The catheter includes an end portion configured to slide over the stem of the inflatable port. The catheter has a lumen in fluid communication with the chamber of the inflatable port when connected to the inflatable port. The catheter lock is configured to slide over the end portion of the catheter over the stem of the inflatable port to lock the catheter on the stem of the inflatable port.

In some embodiments, the bladder is fixed to the housing around the major and minor openings of the chamber. Fixing the bladder to the housing around the major opening of the chamber provides unobstructed needle access to the septum. Fixing the bladder to the housing around the minor opening of the chamber provides fluid communication between the chamber and the stem.

In some embodiments, the bladder is a needle penetrable, self-sealing bladder configured for inflation by way of penetration with a needle and injection with a fluid in a syringe.

In some embodiments, the bladder is a needle penetrable, self-sealing bladder configured for deflation by way of penetration with a needle and withdrawal of a fluid form the bladder into a syringe.

In some embodiments, the fluid is selected from a liquid including water or saline and a gas including air, nitrogen, or argon. In some embodiments, the fluid is sterile saline.

In some embodiments, the housing has a structural integrity for mechanically assisted pressurized injections to achieve a desired flow rate of injectant through the inflatable port.

Also disclosed herein is a method for implanting a catheter assembly including, in some embodiments, obtaining components of the catheter assembly; introducing the catheter to a superior vena cava of a patient through a first incision near a clavicle of the patient; introducing the inflatable port to a port pocket in the patient created through a second incision below the first incision on a chest of the patient; connecting the catheter to the inflatable port and locking the catheter on the stem of the inflatable port; inflating the inflatable port to an appropriately sized port for the patient. The components of the catheter assembly include the inflatable port, the catheter including an end portion configured to slide over a stem of the inflatable port, and a catheter lock configured to slide over the end portion of the catheter over the stem of the inflatable port to lock the catheter on the stem of the inflatable port.

In some embodiments, inflating the inflatable port from a smaller size to a larger size of the inflatable port corresponding to the appropriately sized port for the patient enables the second incision to be a smaller incision than that typically required of existing ports. This minimizes scarring for the patient.

In some embodiments, the method also includes closing the port pocket with sutures about the second incision before inflating the inflatable port.

In some embodiments, the inflatable port includes a housing, a chamber within the housing, a septum over the chamber, a hollow stem extending from the housing, and a bladder around at least a portion of the housing. The chamber has a major opening and a minor opening. The septum is over the major opening of the chamber. The septum is fixed to the housing. The stem fluidly connects to the chamber by way of the minor opening of the chamber. The bladder is a needle penetrable, self-sealing bladder. The bladder is configured to increase a size of the inflatable port upon inflation of the bladder and decrease the size of the inflatable port upon deflation of the bladder.

In some embodiments, the method also includes penetrating the bladder with a needle and injecting the bladder with a fluid from a syringe to inflate the inflatable port.

In some embodiments, the method also includes penetrating the bladder with a needle and withdrawing a fluid from the bladder to deflate the inflatable port. The method also includes removing the inflatable port from the port pocket of the patient after withdrawing the fluid from the bladder.

These and other features of the concepts provided herein will become more apparent to those of skill in the art in view of the accompanying drawings and following description, which disclose particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

With respect to "uninflated," as in an uninflated state of a bladder of an inflatable port, the uninflated state of the bladder includes a state of the bladder in which the bladder has not yet been inflated by a clinician. That is, the bladder in its uninflated state includes the bladder of a newly unpackaged inflatable port. With respect to "inflated," as in an inflated state of the bladder of the inflatable port, the inflated state of the bladder includes a state of the bladder in which at least some fluid has been injected into the bladder by a clinician. That is, the bladder of the inflated port in its inflated state includes at least a partially inflated bladder. When a maximum amount of fluid has been injected into the bladder of the inflatable port, the bladder is "fully inflated." With respect to "deflated," as in a deflated state of the bladder of the inflatable port, the deflated state of the bladder includes a state of the bladder in which at least some fluid has been withdrawn from the bladder by a clinician. That is, the bladder of the inflated port in its deflated state includes at least a partially inflated bladder. Context can determine whether the inflated port is in its inflated state or its deflated state.

Unless defined otherwise, all technical and scientific terms used herein have the same meaning as commonly understood by those of ordinary skill in the art.

A clinician typically strives to minimize incision sizes and port-pocket sizes created in patients when implanting vascular access ports. Correspondingly smaller sized access ports are also chosen to minimize scarring from implanting the ports. Unfortunately, smaller-sized access ports may not always match the body habitus of the patients. This can result in access ports that cannot be located or palpated for infusion-set access.

If larger-sized ports are implanted to avoid locating-and-palpating issues associated with infusion-set access, the larger-sized ports might end up being too large for the patients—particularly following weight loss that is typical for cancer patients if they become cachectic. This can create cosmetic challenges for the patients, as well as possible skin erosion issues.

In view of the foregoing, an access port is needed that minimizes port-placement scarring and avoids the locating-and-palpating issues associated with infusion-set access. Disclosed herein are inflatable ports, catheter assemblies including the inflatable ports, and methods thereof that address at least the foregoing.

Inflatable Ports

Figure 2:
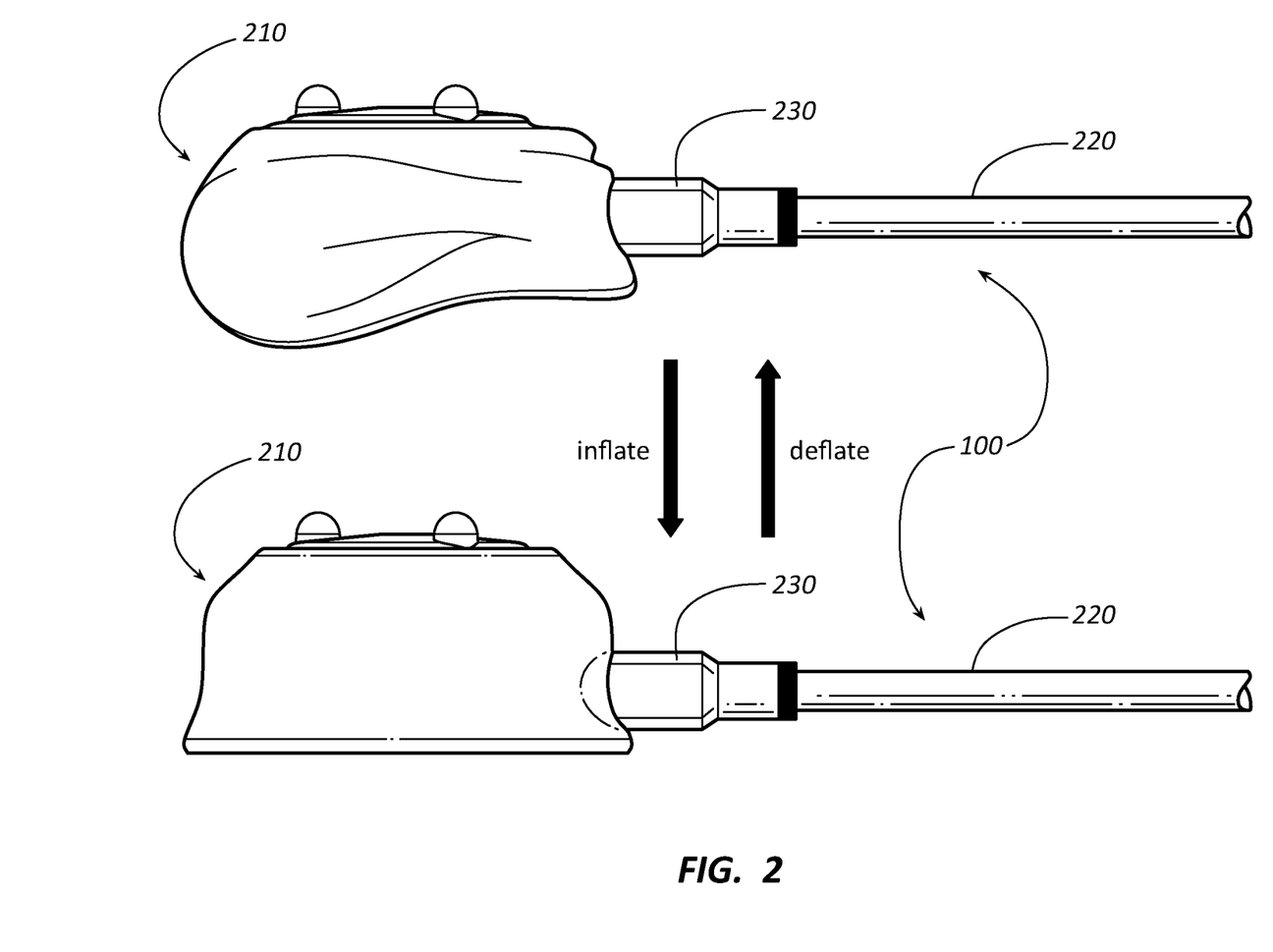
FIG. 2 illustrates a catheter assembly including an inflatable port in an inflated state and the inflatable port in a deflated state in accordance with some embodiments.
Figure 3A:
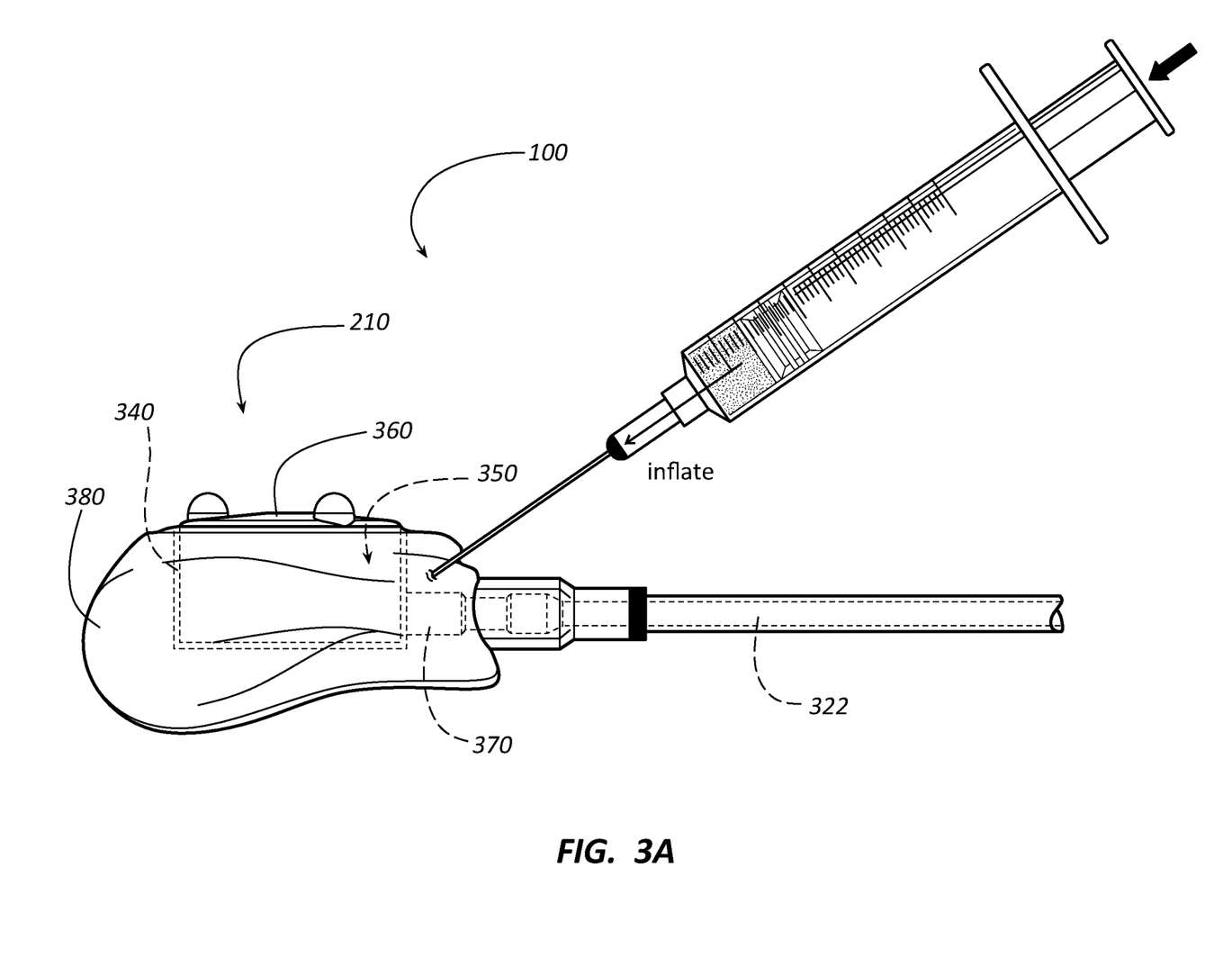
FIG. 3A illustrates inflating an inflatable port in accordance with some embodiments.
Figure 3B:
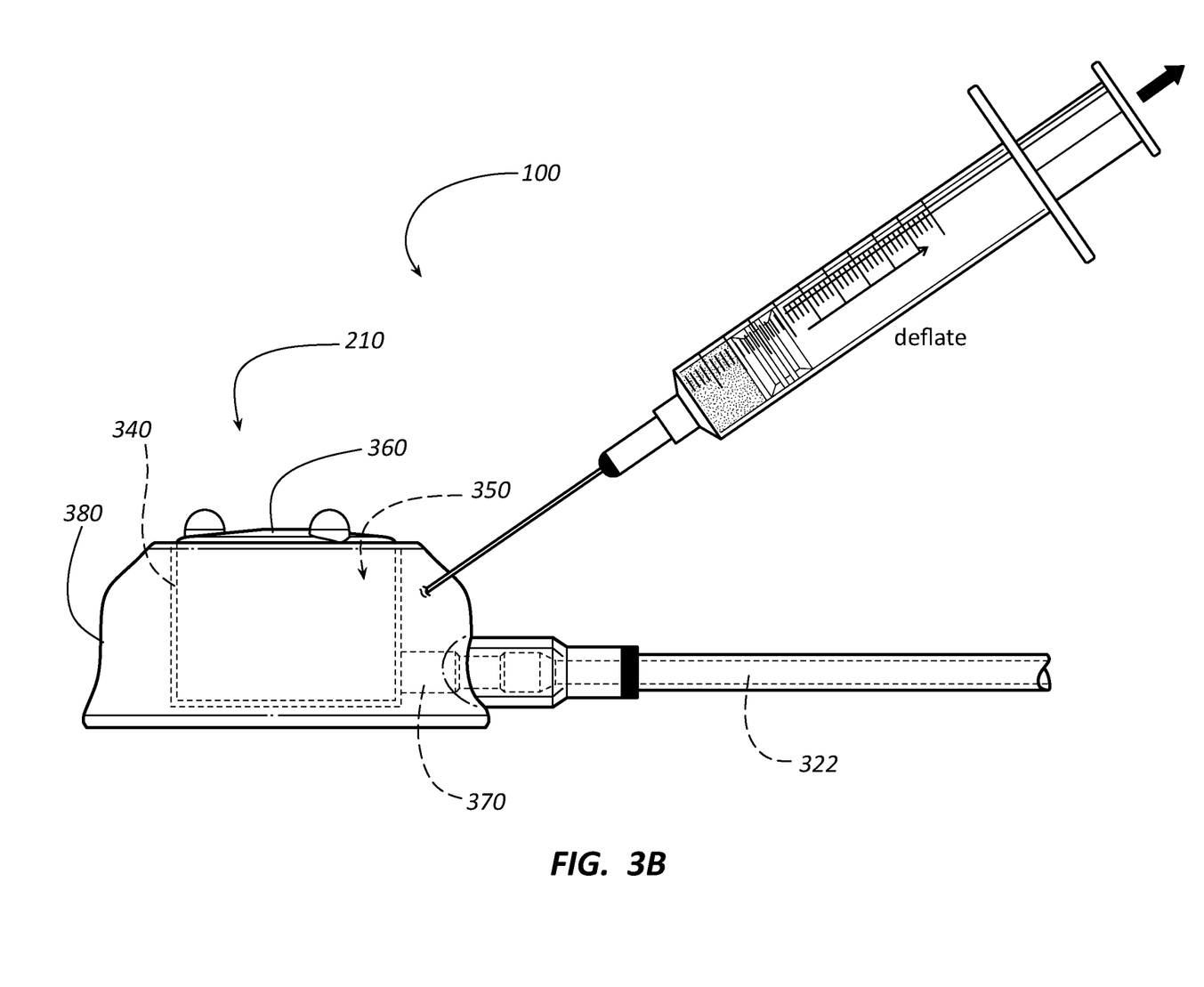
FIG. 3B illustrates deflating an inflatable port in accordance with some embodiments.

As shown in FIGS. 2, 3A, and 3B, an inflatable port 210 can include a housing 340, a chamber 350 within the housing 340, a septum 360 over the chamber 350, a hollow stem 370 extending from the housing 340, and a bladder 380 around at least a portion of the housing 340. The chamber 350 can have a major opening and a minor opening. The septum 360 can be over the major opening of the chamber 350. The septum 360 can be fixed to the housing 340. The stem 370 can fluidly connect to the chamber 350 by way of the minor opening of the chamber 350. The bladder 380 can be configured to increase a size of the inflatable port 210 upon inflation of the bladder 380 and decrease the size of the inflatable port 210 upon deflation of the bladder 380.

The bladder 380 can be fixed to the housing 340 around the major and minor openings of the chamber 350. Fixing the bladder 380 to the housing 340 around the major opening of the chamber 350 provides unobstructed needle access to the septum 360. Fixing the bladder 380 to the housing 340 around the minor opening of the chamber 350 provides fluid communication between the chamber 350 and the stem 370.

As shown in FIGS. 3A and 3B, the bladder 380 can also be a needle penetrable, self-sealing bladder configured for inflation by way of penetration with a needle and injection with a fluid in a syringe. The bladder 380 can also be configured for deflation by way of penetration with a needle and withdrawal of a fluid form the bladder 380 into a syringe.

The fluid for inflating the bladder 380 can be selected from a liquid including water or saline (e.g., sterile saline) and a gas including air, nitrogen, or argon.

The housing 340 can have a structural integrity for mechanically assisted pressurized injections that achieve a desired flow rate of injectant through the inflatable port 210. Mechanically assisted pressurized injection are useful for providing contrast media during computerized tomography ("CT") scans.

The inflatable port 210 can also be configured with one or more radiopaque elements configured for identifying the inflatable port 210 by radiography.

Catheter Assemblies Including Inflatable Ports

As shown in FIGS. 1, 2, 3A, and 3B, a catheter assembly 100 can include the inflatable port 210, a catheter 220 configured to fluidly connect to the inflatable port 210, and a catheter lock 230 configured to lock the catheter 220 on to the inflatable port 210. The inflatable port 210, as set forth above, includes the housing 340, the chamber 350 within the housing 340, the septum 360 over the chamber 350, the hollow stem 370 extending from the housing 340, and the bladder 380 around at least a portion of the housing 340. The catheter 220 includes an end portion configured to slide over the stem 370 of the inflatable port 210. The catheter 220 has a lumen 322 in fluid communication with the chamber 350 of the inflatable port 210 when connected to the inflatable port 210. The catheter lock 230 is configured to slide over the end portion of the catheter 220 over the stem 370 of the inflatable port 210 to lock the catheter on the stem 370 of the inflatable port 210.

The catheter 220 (e.g., the end portion of the catheter 220), the catheter lock 230, or both the catheter 220 and the catheter lock 230 can also be configured with one or more radiopaque elements configured for identifying the inflatable port 210 by radiography.

Methods

A method for implanting the catheter assembly 100 can include obtaining components of the catheter assembly 100; introducing the catheter 220 to a superior vena cava of a patient P (see FIG. 1) through a first incision near a clavicle of the patient P; introducing the inflatable port 210 to a port pocket in the patient P created through a second incision below the first incision on a chest of the patient P; connecting the catheter 220 to the inflatable port 210 and locking the catheter 220 on the stem 370 of the inflatable port 210; inflating the inflatable port 210 to an appropriately sized port for the patient P. Again, the components of the catheter assembly 100 include the inflatable port 210, the catheter 220 including an end portion configured to slide over the stem 370 of the inflatable port 210, and the catheter lock 230 configured to slide over the end portion of the catheter 220 over the stem 370 of the inflatable port 210 to lock the catheter on the stem 370 of the inflatable port 210. The inflatable port 210 includes a housing 340, a chamber within the housing 340, a septum 360 over the chamber, a hollow stem 370 extending from the housing 340, and a bladder 380 around at least a portion of the housing 340.

Figure 1:
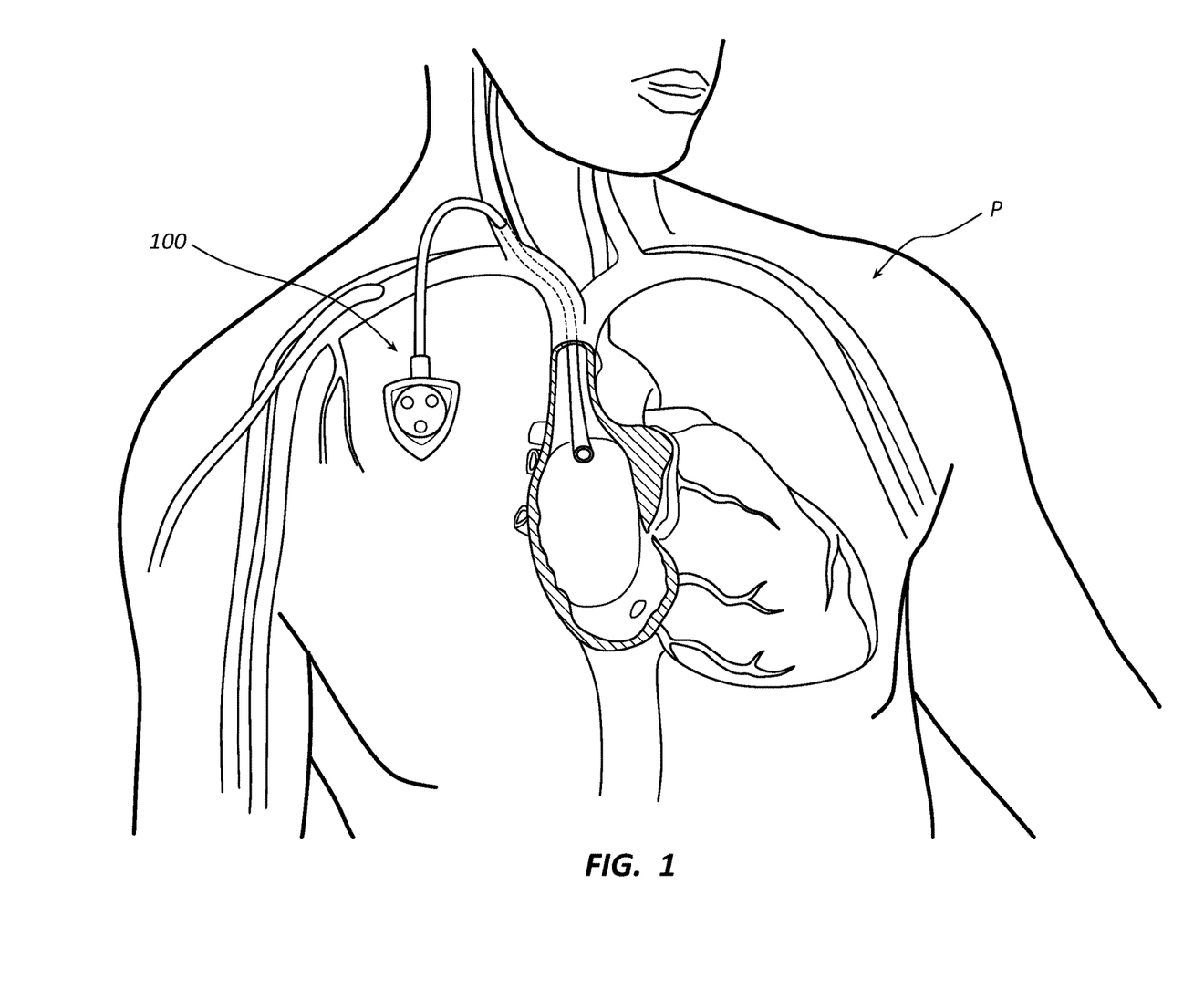
FIG. 1 illustrates a patient with a catheter assembly including an inflatable port in accordance with some embodiments.

Inflating the inflatable port 210 from a smaller size to a larger size of the inflatable port 210 corresponding to the appropriately sized port for the patient P enables the second incision to be a smaller incision than that typically required of existing ports. This minimizes scarring for the patient P.

The method can also include closing the port pocket with sutures about the second incision before inflating the inflatable port 210. The inflatable port 210 can be inflated before closing the port pocket or through the patient's skin once the port pocket has been closed.

The method can also include penetrating the bladder 380 with a needle (e.g., non-coring needle) and injecting the bladder 380 with a fluid from a syringe to inflate the inflatable port 210. This is shown in FIG. 3A.

The method can also include penetrating the bladder 380 with a needle (e.g., non-coring needle) and withdrawing a fluid from the bladder 380 to deflate the inflatable port 210. This is shown in FIG. 3B.

The method also includes removing the inflatable port 210 from the port pocket of the patient after withdrawing the fluid from the bladder 380.

In view of the foregoing, an inflatable port is disclosed having a minimal profile (e.g., a minimal height and width) when uninflated for at least placement during an implantation procedure. Following placement of the inflatable port, the inflatable port can be inflated to increase the height of the inflatable port, the width of the inflatable port, or both. The increase in the size of the inflatable port can provide improved stability as well as an improved ability to locating the inflatable port by way of palpatation. The inflatable port can also be deflated for downsizing of the inflatable port. The decrease in size of the inflatable port can provide an appropriate size of the inflatable port for a patient experiencing weight loss and resulting exposure of the port profile under his or her skin. As such, the inflatable port can be inflated or deflated depending upon particular dimensions needed at a time in the patient's timeline of treatment (e.g., cancer treatment).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An inflatable port, comprising:
a housing;
a chamber in the housing, the chamber having a major opening and a minor opening;
a septum over the major opening of the chamber, the septum fixed to the housing;
a hollow stem extending from the housing, the hollow stem fluidly connected to the chamber by way of the minor opening of the chamber; and
a needle-penetrable, self-sealing bladder around at least a portion of the housing configured to increase or decrease a size of the inflatable port upon a penetration of the bladder with a needle and a subsequent injection with a fluid to increase the size of the inflatable port or a withdrawal of the fluid to decrease the size of the inflatable port.

2. The inflatable port of claim 1, wherein the bladder is fixed to the housing around the major opening and the minor opening of the chamber, thereby providing an unobstructed needle access to the septum and a fluid communication between the chamber and the hollow stem.

3. The inflatable port of claim 1, wherein the fluid is selected from a liquid including water or saline and a gas including air, nitrogen, or argon.

4. The inflatable port of claim 1, wherein the fluid is sterile saline.

5. The inflatable port of claim 1, wherein the housing has a structural integrity for mechanically assisted pressurized injections to achieve a desired flow rate of an injectant through the inflatable port.

6. A catheter assembly, comprising:
a) an inflatable port including:
a housing;
a chamber in the housing, the chamber having a major opening and a minor opening;
a septum over the major opening of the chamber, the septum fixed to the housing;
a hollow stem extending from the housing, the hollow stem fluidly connected to the chamber by way of the minor opening of the chamber; and
a needle-penetrable, self-sealing bladder around at least a portion of the housing configured to increase or decrease a size of the inflatable port upon a penetration of the bladder with a needle and a subsequent injection with a fluid to increase the size of the inflatable port or a withdrawal of the fluid to decrease the size of the inflatable port;
b) a catheter including an end portion configured to slide over the hollow stem of the inflatable port, the catheter having a lumen in fluid communication with the chamber of the inflatable port; and
c) a catheter lock configured to slide over the end portion of the catheter over the hollow stem of the inflatable port, thereby locking the catheter on the hollow stem of the inflatable port.

7. The catheter assembly of claim 6, wherein the bladder is fixed to the housing around the major opening and the minor opening of the chamber, thereby providing an unobstructed needle access to the septum and a fluid communication between the chamber and the hollow stem.

8. The catheter assembly of claim 6, wherein the fluid is selected from a liquid including water or saline and a gas including air, nitrogen, or argon.

9. The catheter assembly of claim 6, wherein the fluid is sterile saline.

10. The catheter assembly of claim 6, wherein the housing has a structural integrity for mechanically assisted pressurized injections to achieve a desired flow rate of an injectant through the inflatable port.

11. A method for implanting a catheter assembly, the method comprising:
obtaining components of the catheter assembly, wherein the components include:
a) an inflatable port including:
a housing;
a chamber in the housing, the chamber having a major opening and a minor opening;
a septum over the major opening of the chamber, the septum fixed to the housing;
a hollow stem extending from the housing, the hollow stem fluidly connected to the chamber by way of the minor opening of the chamber; and
a needle-penetrable, self-sealing bladder around at least a portion of the housing configured to increase or decrease a size of the inflatable port upon a penetration of the bladder with a needle and a subsequent injection with a fluid to increase the size of the inflatable port or a withdrawal of the fluid to decrease the size of the inflatable port;
b) a catheter including an end portion configured to slide over the hollow stem of the inflatable port; and
c) a catheter lock configured to slide over the end portion of the catheter over the hollow stem of the inflatable port to lock the catheter on the hollow stem of the inflatable port;
introducing the catheter to a superior vena cava of a patient through a first incision near a clavicle of the patient;
introducing the inflatable port to a port pocket in the patient created through a second incision below the first incision on a chest of the patient;
connecting the catheter to the inflatable port and locking the catheter on the hollow stem of the inflatable port; and inflating the inflatable port to an appropriately sized port for the patient.

12. The method of claim 11, wherein the inflating the inflatable port from a smaller size to a larger size of the inflatable port corresponding to the appropriately sized port for the patient minimizes scarring for the patient.

13. The method of claim 11, further comprising closing the port pocket with sutures about the second incision before the inflating the inflatable port.

14. The method of claim 11, further comprising penetrating the bladder with the needle and injecting the bladder with the fluid from a syringe to inflate the inflatable port.

15. The method of claim 11, further comprising penetrating the bladder with the needle and withdrawing the fluid from the bladder to deflate the inflatable port, and removing the inflatable port from the port pocket of the patient.

* * * * *